United States Patent
Tate et al.

(10) Patent No.: US 8,758,737 B2
(45) Date of Patent: Jun. 24, 2014

(54) EVAPORATIVE COOLING COMPOSITION

(71) Applicants: Carl Patrick Tate, Gordon, TX (US);
Kerri Lynn Tate, Gordon, TX (US);
Albert Scott Adamson, Plano, TX (US)

(72) Inventors: Carl Patrick Tate, Gordon, TX (US);
Kerri Lynn Tate, Gordon, TX (US);
Albert Scott Adamson, Plano, TX (US)

( * ) Notice: Subject to any disclaimer, the term of this patent is extended or adjusted under 35 U.S.C. 154(b) by 0 days.

(21) Appl. No.: 13/677,107

(22) Filed: Nov. 14, 2012

(65) Prior Publication Data

US 2013/0072571 A1    Mar. 21, 2013

Related U.S. Application Data

(63) Continuation of application No. 11/482,289, filed on Jul. 7, 2006.

(60) Provisional application No. 60/702,848, filed on Jul. 28, 2005.

(51) Int. Cl.
*A61K 31/74*    (2006.01)
*A61K 31/045*    (2006.01)

(52) U.S. Cl.
USPC ............... 424/78.05; 424/78.03; 514/724

(58) Field of Classification Search
None
See application file for complete search history.

*Primary Examiner* — Bethany Barham
*Assistant Examiner* — Jeffrey T Palenik
(74) *Attorney, Agent, or Firm* — Thrasher Associates

(57) ABSTRACT

A liquid evaporative cooling composition has been discovered which is peculiarly effective in providing relief from heat-related discomfort. The composition utilizes a concentrate, dissolved in water, which preferably consists essentially of (a) about forty-three percent by weight of an alcohol; (b) about twelve percent by weight of a surfactant; (c) about four percent by weight of an aromatic oil; (d) about one percent by weight of a cooling agent; and (e) about forty percent by weight of water.

Various ranges of concentrations for the composition components have been discovered, the concentration ranges featuring various advantages and disadvantages, and these ranges are disclosed herein.

The composition can be applied to the surface to be cooled (typically, a user's skin) in a number of ways and has even been found to relieve heat-related discomfort in animals.

8 Claims, No Drawings

EVAPORATIVE COOLING COMPOSITION

CROSS-REFERENCE TO RELATED APPLICATIONS

This application claims the benefit of (and incorporates by reference the entirety of):
U.S. Provisional Patent Application No. 60/702,848, filed Jul. 28, 2005 (entitled "A Cooling Agent for Humans and Other Mammals").

FIELD OF THE INVENTION

This invention relates generally to evaporative cooling products for use by or on humans and animals.

BACKGROUND OF THE INVENTION

The Insidious Killers: Heat Stroke and Dehydration.

Ordinarily, our bodies make up for the water we lose. However, unfortunately, two extremely common heat-related disorders continue to occur all to frequently in our society, conditions which can be life-threatening if undiagnosed or untreated: dehydration and heat stroke.

Although these maladies can occur anywhere, they are most commonly encountered, in the United States for example, in the southern states during the summer months when outdoor activity is at a premium.

Dehydration most commonly occurs as a result of exposure to heat, although it can also easily occur as a dangerous side-effect of diarrhea, vomiting, and fever. In this respect, it is particularly dangerous to both children and the elderly.

When we are healthy, we drink plenty of fluids, eat healthy foods (containing water), and we watch our exposure to heat. The water we take in is roughly matched by the water we lose through urine, stool, sweat, and tears. However, when we are overexposed to heat, or we experience fever, diarrhea, or vomiting due to illness, then we may lose more water than we take in and dehydration can occur. The dehydration process is accelerated if we are engaged in high-intensity activity out of doors, as our body sweats more and we lose even more water, more rapidly, through our body's natural cooling process (i.e., sweating).

When dehydration occurs, we experience thirst, less-frequent urination, dry skin, fatigue, light-headedness, dizziness, fever, tearless crying, and increased heart rate and breathing. These symptoms are the signs our body uses to tell us we're in trouble.

Treatment for dehydration differs based upon the cause and severity of the malady. However, in the case of mild dehydration, the most common recommendations are: (a) rehydration through the consumption/drinking of fluids such as water and/or other commercially offered electrolytic fluids; (b) rehydration through the use of an intravenous fluid line (an "IV") to directly and quickly rehydrate the body in more severe cases; and (c) reduction of the heat load (i.e., the activity level and heat exposure) the person is experiencing.

Heat stroke is the most severe form of heat-related illness, and, in fact, it is a life-threatening emergency condition. In a nutshell, heat stroke occurs as a result of a long, extreme exposure to the sun under circumstances in which the person simply doesn't sweat enough (or effectively enough) to maintain a stable, healthy body temperature. The reason for the focus on the process of sweating is that this is one of the key ways in which our body cools itself; basically, the body radiates heat, which is convectively cooled by the movement of the air around us (aided significantly by the occurrence of a simple breeze), and it also sweats, creating a mechanism for natural evaporative phase-change cooling as the water in our sweat evaporates.

However, if the heat is extreme, the humidity is high (which reduces the instances of and effectiveness of evaporative cooling), our activity levels are excessive, or our body's water level is low, or any combination of these conditions occurs, then our body may fall behind in its discharge of excess heat, and the continued buildup of excessive heat and temperature can then occur, ultimately threatening the person's life through the occurrence of a heat stroke.

The following are some of the most common symptoms of heat stroke: high body temperature, flushed dry skin, headache, fatigue, dizziness, disorientation, hallucinations, rapid heartbeat, seizure, and loss of consciousness.

It is important for the heat stroke victim to be treated immediately. Standard first aid treatments focus heavily upon getting the person's body temperature down by removing excess clothing, applying, cool water and/or ice packs to the skin and trunk and groin areas, as well as elevating the feet.

The invention disclosed herein should NEVER be confused with treatment by a physician for the clinical conditions of dehydration or heat stroke; neither should it be confused as a source of first aid for those conditions.

However, what it does provide is a preventive mechanism for preventing heat exhaustion and other heat-related illnesses. That is, it provides a mechanism for effectuating local cooling of a person's (or animal's) local, mild elevated skin temperature. The presence of the aromatic components also not only relieves the sinuses, and various other allergic conditions, but, in addition, also provides relief from the temporary lightheadedness that can occur in heated conditions.

Cooling of the sort effectuated by means of this invention, combined with a healthy, sustained intake of appropriate fluids, alongside sensible, prudent management of physical activities (and breaks), and attention to the heat conditions under which those activities are undertaken, should help one to more safely and happily enjoy activities outdoors.

BRIEF SUMMARY OF THE INVENTION

A liquid evaporative cooling composition has been discovered which is peculiarly effective in providing relief from heat-related discomfort. The composition utilizes a concentrate, dissolved in water, which preferably consists essentially of (a) about forty-three percent by weight of an alcohol; (b) about twelve percent by weight of a surfactant; (c) about four percent by weight of an aromatic oil; (d) about one percent by weight of a cooling agent; and (e) about forty percent by weight of water.

Various ranges of concentrations for the composition components have been discovered, the concentration ranges featuring various advantages and disadvantages, and these ranges are disclosed herein.

The composition can be applied to the surface to be cooled (typically, a user's skin) in a number of ways and has even been found to relieve heat-related discomfort in animals.

BRIEF DESCRIPTION OF THE SEVERAL VIEWS OF THE DRAWINGS

No drawings are necessary for the understanding of this disclosure.

DETAILED DESCRIPTION OF THE INVENTION

This application claims the benefit of (and incorporates by reference the entirety of) U.S. Provisional Patent Application No. 60/702,848, filed Jul. 28, 2005 (entitled "A Cooling Agent for Humans and Other Mammals").

A novel liquid evaporative cooling composition.

A liquid evaporative cooling composition has been discovered which is peculiarly effective in providing relief from heat-related discomfort. The composition utilizes a concentrate which comprises: (a) between about ten percent and about ninety percent by weight of an alcohol; (b) between about one percent and about eighty percent by weight of a surfactant; (c) between about one-tenth of one percent and about fifteen percent by weight of an aromatic oil; (d) between about one-tenth of one percent and about sixteen percent by weight of a cooling agent; and (e) between about one percent and about ninety percent by weight of water.

The concentrate is then dissolved in a water-based solvent, and the resulting composition is applied to the skin so as to provide an evaporative and pharmacologic cooling effect.

The dilution ratio of the concentrate to the water-based solvent is volume based, and is preferably 1.5-3.5 ounces per gallon. Even more preferred is the range of 1.75-3.25 ounces per gallon. Most preferred is the range 2-3 ounces per gallon with 2.5 ounces per gallon being viewed as the optimum (although 2-3 ounces per gallon effectuates an extraordinarily high-quality commercial product).

A comment about each of the concentration components is in order.

The alcohol is preferably ethyl alcohol (CAS# 64-17-5). It is provided in the composition to provide an instantaneous to medium-term cooling effect due to the rapid evaporation of alcohol (note: alcohols of this sort maintain a vapor pressure of at or about 41.0 mmHg). The alcohol also helps solubilize the cooling agents and fragrances into this water-containing composition. The alcohol also provides an antiseptic and antibacterial function in the finished product when used on the skin.

The preferred alcohol is denatured alcohol 40-B (also known in the chemical industry as 40-2) as specified in Title 27 of the Code of Federal Regulations (CFR), Ch.1, Subpart D, Sec. 21-76, Formula No, 40B. This is a standard alcohol used by the fragrance industry. It is denatured with tert. butyl alcohol (⅛th of a gallon) and denatonium benzoate (Bitrex) (¹⁄₁₆th of an avoirdupois ounce per 100 gallons of ethyl alcohol).

Other denatured alcohols can be used in place of SD 40-B, but with some potential disadvantages. For example, SD Alcohol 39-C (a prior fragrance industry standard alcohol) can be used, but the denaturant is 1 gallon of diethyl phthalate per 100 gallons of alcohol. And some companies and consumers have reported that diethyl phthalate leaves a slight, unpleasant film on the skin.

Most other denatured alcohols could also be used, but many contain odorous materials as the denaturant which would potentially interfere with the scent/aroma/aromatic impact of this product. Ethyl alcohol can also be used; however, the alcohol tax would be cost prohibitive.

Other alcohols like isopropyl alcohol could be used but, again, there are some potential slight disadvantages. For example, isopropyl alcohol would likely impart an odor (making the product somewhat less pleasant to use) or a lower cooling index (e.g., isopropyl alcohol with a vapor pressure of 310 mmHg).

The concentration of alcohol used in the composition is important. The higher the alcohol level, the more dramatic the cooling effect. However, with higher alcohol levels, there will also frequently be greater irritation/drying effects to the skin. Conversely, if the alcohol level is too low, the cooling effect will be minimal, and it may not totally solubilize the cooling agents and fragrances into the water.

Thus, it is believed that the broad range specified above (i.e., from about ten percent to ninety percent by weight) for the concentrate is indeed effective, but, as one exceeds ninety percent, irritative/drying effects on the skin become an increasing source of concern and hence diminish the efficacy and overall utility of the product to the end user. Furthermore, at these high levels of concentration, the cooling effect would be so exaggerated that it could even be somewhat uncomfortable.

Thus, an alternative embodiment, which is even more attractive in terms of its overall utility to the user, is one which utilizes a concentrate comprising: (a) said alcohol in a concentration of between about twenty-five percent and about seventy-five percent by weight; (b) said surfactant present in a concentration of between about five percent and about thirty percent by weight; (c) said aromatic oil present in a concentration of between about one-half of one percent and about ten percent by weight; (d) said cooling agent present in a concentration of between about one-half of one percent and about eleven percent by weight; and (e) said water present in a concentration of between about ten percent and about seventy-five percent by weight.

This moderated range of concentrations is believed to be much more effective than the workmanlike range specified above. Cooling and solubilization are not optimized in this range, but irritation/drying will be moderated (although still suboptimal to some portion of the population).

A superior alternative embodiment for the concentrate comprises the following: (a) alcohol present in a concentration of between about forty percent and about fifty percent by weight; (b) surfactant present in a concentration of between about ten percent and about twenty percent by weight; (c) aromatic oil present in a concentration of between about one percent and about five percent by weight; (d) cooling agent present in a concentration of between about two percent and about five percent by weight; and (e) water present in a concentration of between about thirty percent and about fifty percent by weight.

This embodiment provides perhaps the practical optimum in terms of cooling effect in that it provides instantaneous relief without creating a sensation that is uncomfortably cold. It also provides sufficient solvent properties to help solubilize the cooling agents and fragrances to allow the product to remain free and clear of ingredient separation with the addition of water. Also, this alcohol level is sufficiently low that it is very likely not going to be perceived as irritating or drying to the skin in the majority of the population.

As a result of experimentation, the following has been deemed a good and effective target composition for the composition concentrate: (a) alcohol present in a concentration of about forty-three percent by weight (note: 43.2% has been used with great success); (b) surfactant present in a concentration of about twelve percent by weight (note: 12.0% has been used with great success); (c) aromatic oil present in a concentration of about four percent by weight (note: 3.6% has been used with great success); (d) cooling agent present in a concentration of about one percent by weight (note: 1.2% has been used with great success); and (e) water present in a concentration of about forty percent by weight (note: 40.0% has been used with great success).

While it is believed that the compositions described above are resilient to the addition of other ingredients (ingredients which are inert in their effect upon the fulfillment of the objectives of the invention), it should also be noted that many other compositions doubtless exist which feature other ingredients which fundamentally alter the desired physical chemistry. Thus, care will be exercised by those of ordinary skill in the art in making and using the composition described above.

Regarding the non-alcoholic components of the composition, the surfactant is preferably polyoxyethylene sorbitan monolaurate (CAS# 9005-64-5).

To understand why a surfactant is needed, one must understand that fragrance chemicals, fragrance oils and essential oils are generally insoluble in water. The reason: since they are all based on carbon chemistry, as a general rule, they tend to be only soluble in oils and or other carbon-containing compounds (i.e., they are "hydrophobic").

Separation or cloudiness in a product when a fragrance oil is used indicates insolubility of the fragrance and/or cooling agent in that product. Although a solvent like alcohol can be used to help dissolve a fragrance oil in water and form a true solution, it is not preferred to use too much alcohol as a solvent in these kinds of products because of the increased drying effect it has on the skin and the increased flammability of the solution.

Solubilization can be obtained by the colloidal dispersion of the menthol component and spearmint oil component in water through use of a surfactant. The mechanism involved is the reduction of the interfacial tension between these materials and the water in the system. The surfactant must disperse in water to give a clear solution, and the menthol and spearmint oil must disperse and dissolve, to produce a clear solution in the surfactant system.

Suitable substitute surfactants for this system would include: polyoxyethylene isohexadecyl ether, polyoxyethylene fatty esters, ethoxylated hydrogenated castor oil, isocetyl acetate, polyoxyethylene polyoxypropylene cetaryl ether, caprylic/capric triglyceride, polyoxyethylene sorbitan oleate, alkanolamide, polyoxyethylene tridecyl alcohol, sorbitan trioleate, octylphenyloxy-polyethoxyethanol, polyoxyethylene sorbitan fatty esters, and ethoxylated oleyl ethers. Notably, the surfactant used in this system must be non toxic and skin safe.

The preferred surfactant chosen for this application, as stated hereinabove, is polyoxyethylene sorbitan monolaurate, a polyoxyethylene fatty ester. Trade names for this surfactant are Polysorbate 20 and Tween 20.

The aromatic oil is preferably *menthe viridis* (spearmint) leaf oil, although peppermint oil (*meritha piperata* L.), cornmint oil (*mentha arvensis* L.), spike lavender oil, citrus, masculine fragrance (parfume), feminine fragrance (parfume), and fresh scent (clean soap aroma), all fragrances well known by these cognomens in the industry, can also be used.

Spearmint oil was chosen as the preferred fragrance for this blend due to its "refreshing" character. It is also easily recognized and well accepted by the general population. It is also used as a flavor and is non-toxic.

The preferred cooling agent is L-menthol (CAS# 89-78-1) although persons of ordinary skill in the art will immediately recognize a host of cooling agents which would easily serve as substitutes for L-menthol.

L-Menthol (laevo-Menthol) is an ingredient known for its cooling and antibacterial properties. When applied to an affected area, it rapidly cools the tendons and muscles. It causes dilation in the blood vessels that carry blood to the joints, increasing blood flow and reducing swelling.

The reason Menthol provides a cooling sensation is that it reacts with thermo-receptors in the skin and triggers nerve cells in that area to sense cold even though the temperature does not change. Menthol works as a local anesthetic and provides relief from itching by providing a thermal sensation to replace the irritation.

Other cooling agents which would serve as potential suitable replacements for L-Menthol would include: menthone, herboxide, iso-menthone, iso-pulegol acetate, l-menthone, 2-sec-butylcyclohexanone (CAS# 14765-304), and isobornyl formate.

The water used is preferably filtered water, although unfiltered water will also likely be effectual.

Using the Novel Liquid Evaporative Cooling Composition.

The novel cooling composition can be physically applied so as to be effective in effectuating cooling in a number of ways.

Direct application entails pouring or squirting the composition onto the skin surface. The advantage of this method of application is its simplicity. Jars or other containers (e.g., squeeze bottles) of the composition not only serve as a long-term storage mechanism; in addition, they facilitate this kind of simple, direct application of the composition. The disadvantage, of course, is that it is easy to over-pour or over-apply the composition resulting in runoff, waste or loss of the material.

Static surface-to-surface applicators can also be used, and these result in both effective contact and reduction of waste. Simply stated, wipes and/or pads (or even sponge shammies, towels, or rags), previously submerged in or coated with the composition, can be applied to the body, and, as the composition evaporates, cooling is effected.

Dynamic surface-to-surface applicators can also be used. The most common type (but by no means the only type) of applicator that would be effective for this purpose is a painter's roller-style device. An effective amount of the cooling composition is applied to the surface of the roller, and then the roller is applied to the skin surface the same way a painter would apply a coat of paint to a wall. The result: a relatively uniform film of the cooling composition, applied quickly to a large block of the target surface area, with minimal waste. Not surprisingly, other components of the typical painter's arsenal can also be used (e.g., conventional brush-type devices and sponge brush-type devices).

Finally, atomizers such as spray bottles, mist fans, misters, aerosol canisters, and or other types of liquid atomizers, whether pressurized or mechanical in operation, can be used to create and direct a fine mist of the product to the skin surface of the user.

The goal of all of the application mechanisms listed above is to maximize the cooling effect of the composition by maximizing the effective heat transfer surface areas for both conduction (from the skin surface to the composition) and evaporation (from the composition in the liquid state to the gaseous state).

The effectiveness of all of the above-referenced delivery mechanisms is enhanced if the composition is cooled prior to application. That is, if the atomizers, wipes or towels are maintained in a cooler at a temperature lower than ambient air and/or lower than the user's skin temperature, then the simple conduction effect associated with the application of this physically cooler mixture to the skin will also effectuate cooling.

The Benefits Of the Invention.

The benefits of use of the novel cooling composition are several. First, and chiefly, use of the invention effectuates rapid cooling of the skin temperature (and ultimately the core body temperature) of the user. Second, the presence of the cooling agents (e.g., the menthol, spearmint scents, etc:) effectuates a clearing of the sinuses and nasal passages which facilitates steady breathing. Third, the presence of the cooling agents imparts a clearing of the sensory faculties generally which imparts additional benefits to the user experiencing heat-related distress, Also, although humans will always be prime users of the invention, the novel cooling composition can also be used to comfort horses, livestock, domestic animals (e.g., the family dog or cat), or, indeed, any other land-based animal or mammal with exposed skin for which an evaporative cooling product would be effective. Thus, it may be used on horses and dogs to protect them from overheating during conventional activities and also to protect thoroughbreds during racing events. Any animal that has experienced heat-related distress can be quickly returned to peak performance for competition.

Although the invention has been described with reference to one or more preferred embodiments, this description should not be construed in a limiting sense. Rather, various improvements, modifications, and additions to the disclosed embodiments, which do not depart from the spirit and scope of the present invention, will become apparent to persons of ordinary skill in the art, and these improvements, modifications and additions, and their equivalents, are to be viewed as being within the ambit of the invention as defined and claimed below.

The invention claimed is:

1. A liquid evaporative cooling composition, consisting of
between about ten percent and about ninety percent by weight of a denatured alcohol;
between about one percent and about eighty percent by weight of a surfactant;
between about one-tenth of one percent and about sixteen percent by weight of a cooling agent; and
between about one percent and about ninety percent be weight of water.

2. The liquid evaporative cooling composition of claim 1 wherein:
said alcohol is present in a concentration of between about twenty-five and about seventy-five percent by weight;
said surfactant is present in a concentration of between about five percent and about thirty-percent by weight;
said cooling agent is present in a concentration of between about one-half percent and about eleven percent by eight; and
said water is present in a concentration of between about ten-percent and about seventy- five percent by weight.

3. The liquid evaporative cooling composition of claim 2 wherein:
said alcohol is present in a concentration of between about forty percent and about fifty percent by weight;
said surfactant is present in a concentration of between about ten percent and about twenty percent of weight;
said cooling agent is present in a concentration of between about two percent and about five percent of weight; and
said water is present in a concentration of between about thirty percent and about fifty percent of weight.

4. The liquid evaporative cooling composition of claim 3 wherein:
said alcohol is present in a concentration of about forty-three percent by weight;
said surfactant is present in a concentration of about twelve percent by weight;
said alcohol is present in a concentration of about forty-three percent by weight;
said cooling agent is present in a concentration of about one percent by weight; and
said water is present in a concentration of about forty percent by weight.

5. A liquid evaporative cooling composition consisting of:
between about ten percent and about ninety percent by weight of a denatured alcohol;
between about one percent and about eighty percent by weight of a surfactant;
between about one-tenth of one percent and about fifteen percent by weight of an aromatic oil;
between about one-tenth percent and about sixteen percent by weight of a cooling agent; and
between about one percent and about ninety percent by weight of water.

6. The liquid evaporate cooling composition of claim 5, wherein:
said alcohol is present in a concentration of between about twenty-five percent and about seventy-five percent by weight;
said surfactant is present in a concentration of between about five percent and about thirty percent by weight;
said aromatic oil is present in a concentration of between about one-half percent and about ten percent by weight;
said cooling agent is present in a concentration of between about one-half percent and about eleven percent by weight; and
said water is present in a concentration of between about ten percent and about seventy-five percent by weight.

7. The liquid evaporate cooling composition of claim 6, wherein:
said alcohol is present in a concentration of between about forty percent and about fifty percent be weight;
said surfactant is present in a concentration of between about ten percent and about twenty percent be weight;
said aromatic oil is present in a concentration of between about one percent and about five percent be weight;
said cooling agent is present in a concentration of between about two percent and about five percent be weight; and
said water is present in a concentration of between about thirty percent and about fifty percent be weight.

8. The liquid evaporative cooling composition of claim 7 wherein:
said alcohol is present in a concentration of about forty-three percent by weight;
said surfactant is present in a concentration of about twelve by weight;
said aromatic oil is present in a concentration of about four percent by weight;
said cooling agent is present in a concentration of about one percent by weight; and
said water is present in a concentration of about forty percent by weight.

* * * * *